(12) United States Patent
Altmann et al.

(10) Patent No.: US 10,792,087 B2
(45) Date of Patent: Oct. 6, 2020

(54) HIGHLIGHTING REGION FOR RE-ABLATION

(71) Applicant: BIOSENSE WEBSTER (ISRAEL) LTD., Yokneam (IL)

(72) Inventors: Andres Claudio Altmann, Haifa (IL); Assaf Govari, Haifa (IL)

(73) Assignee: Biosense Webster (Israel) Ltd., Yokneam (IL)

( * ) Notice: Subject to any disclaimer, the term of this patent is extended or adjusted under 35 U.S.C. 154(b) by 452 days.

(21) Appl. No.: 15/720,650

(22) Filed: Sep. 29, 2017

(65) Prior Publication Data
US 2019/0099211 A1    Apr. 4, 2019

(51) Int. Cl.
*A61B 18/12* (2006.01)
*A61B 18/14* (2006.01)
(Continued)

(52) U.S. Cl.
CPC ............ *A61B 18/12* (2013.01); *A61B 5/0095* (2013.01); *A61B 5/04* (2013.01); *A61B 5/0402* (2013.01); *A61B 5/044* (2013.01); *A61B 5/0422* (2013.01); *A61B 5/053* (2013.01); *A61B 5/0538* (2013.01); *A61B 5/061* (2013.01); *A61B 5/062* (2013.01); *A61B 5/065* (2013.01); *A61B 5/6852* (2013.01); *A61B 5/7235* (2013.01); *A61B 5/7271* (2013.01); *A61B 5/743* (2013.01); *A61B 5/7425* (2013.01); *A61B 5/7435* (2013.01); *A61B 18/1492* (2013.01); *A61B 5/4848* (2013.01); *A61B 5/6853* (2013.01); *A61B 5/6856* (2013.01); *A61B 5/7203* (2013.01);
(Continued)

(58) Field of Classification Search
CPC ...... A61B 18/1482; A61B 2018/00023; A61B 2018/00339; A61B 2018/00577; A61B 2018/00791
See application file for complete search history.

(56) References Cited

U.S. PATENT DOCUMENTS

| | | |
|---|---|---|
| 5,391,199 A | 2/1995 | Ben-Haim |
| 5,443,489 A | 8/1995 | Ben-Haim |

(Continued)

OTHER PUBLICATIONS

European Search Report for corresponding EPA No. 18197464.3 dated Nov. 30, 2018.
(Continued)

*Primary Examiner* — Michael F Peffley
*Assistant Examiner* — Tigist S Demie

(57) ABSTRACT

A method for assessing a lesion formed between first and second regions of body cavity tissue, the method including using a first probe in contact with the tissue at a stimulus location in the first region, and applying to the tissue or sensing in the tissue a first activation signal having a first activation peak at a first time. Respective second activation signals having respective second activation peaks following the first activation signal are received from a second probe having multiple electrodes in contact with the tissue at respective sensing locations in the second region, and based on a temporal relation between the first and second activation peaks and a spatial relation between the stimulus location and the sensing locations, one of the multiple electrodes proximal to a gap in the lesion is identified. A map of the body cavity is displayed with the identified electrode marked on the map.

10 Claims, 5 Drawing Sheets

(51) Int. Cl.
*A61B 5/00* (2006.01)
*A61B 5/042* (2006.01)
*A61B 5/053* (2006.01)
*A61B 5/0402* (2006.01)
*A61B 5/04* (2006.01)
*A61B 5/06* (2006.01)
*A61B 5/044* (2006.01)
*A61B 18/00* (2006.01)
*A61B 34/20* (2016.01)
*A61B 17/00* (2006.01)

(52) U.S. Cl.
CPC ............... *A61B 2017/00084* (2013.01); *A61B 2018/0022* (2013.01); *A61B 2018/00238* (2013.01); *A61B 2018/00351* (2013.01); *A61B 2018/00577* (2013.01); *A61B 2018/00636* (2013.01); *A61B 2018/00702* (2013.01); *A61B 2018/00839* (2013.01); *A61B 2018/00875* (2013.01); *A61B 2018/1435* (2013.01); *A61B 2018/1467* (2013.01); *A61B 2034/2051* (2016.02); *A61B 2034/2053* (2016.02); *A61B 2560/0468* (2013.01); *A61B 2562/04* (2013.01); *A61B 2562/06* (2013.01)

(56) References Cited

U.S. PATENT DOCUMENTS

| | | |
|---|---|---|
| 5,558,091 A | 9/1996 | Acker et al. |
| 5,944,022 A | 8/1999 | Nardella et al. |
| 5,983,126 A | 11/1999 | Wittkampf |
| 6,172,499 B1 | 1/2001 | Ashe |
| 6,177,792 B1 | 1/2001 | Govari et al. |
| 6,456,864 B1 | 9/2002 | Swanson et al. |
| 6,690,963 B2 | 2/2004 | Ben-Haim et al. |
| 6,788,967 B2 | 9/2004 | Ben-Haim et al. |
| 2003/0028183 A1 | 2/2003 | Sanchez et al. |
| 2007/0198007 A1 | 8/2007 | Govari et al. |
| 2015/0011843 A1* | 1/2015 | Toth .................. A61N 1/36185 600/301 |
| 2015/0038824 A1 | 2/2015 | Lupotti |
| 2015/0342662 A1 | 12/2015 | Bustan et al. |
| 2016/0183824 A1* | 6/2016 | Severino ................ A61B 5/044 600/523 |

OTHER PUBLICATIONS

Medical Saint Jude: "EnSite (TM) Velocity (TM) System", Dec. 7, 2016, XP055524455, Retrieved from the Internet: URL: https://www.sjmglobal.com/-/media/galaxy/hcp/media-files/ensite-velocity-handbook-final.pdf:la=en-int.

* cited by examiner

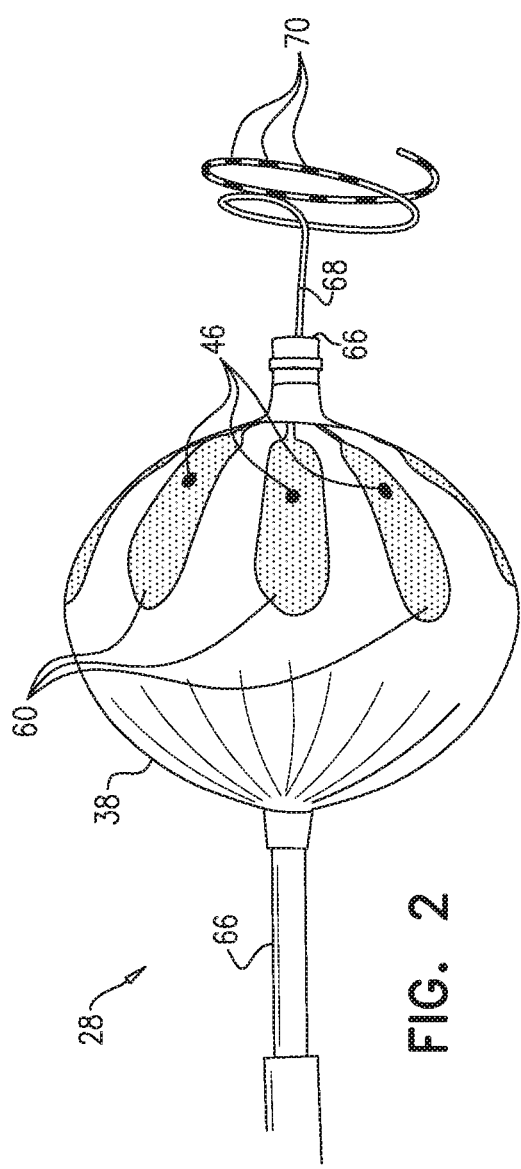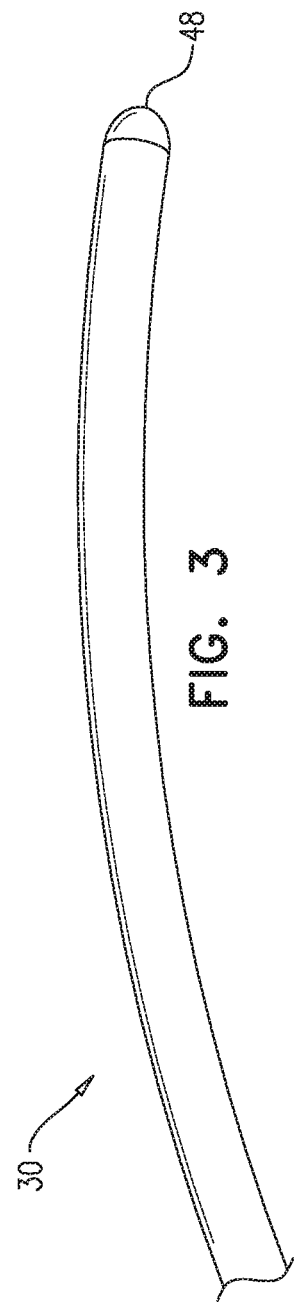

HIGHLIGHTING REGION FOR RE-ABLATION

FIELD OF THE INVENTION

The present invention relates generally to tissue ablation, and specifically identifying a region of body tissue for re-ablation.

BACKGROUND OF THE INVENTION

Arrhythmias are abnormal heart rhythms that are typically caused by a small area of cardiac tissue that produces irregular heartbeats. Cardiac ablation is a medical procedure that can be performed to treat an arrhythmia by destroying the area of the cardiac tissue causing the irregular heartbeats.

U.S. Patent Application 2003/0028183 to Sanchez et al. describes a method for electrophysiologic measuring endpoints of ablation lesions created in fibrillating substrates. The method measures, during an ablation procedure that produces a lesion, electrical activity in cardiac tissue in proximity to the lesion, and then compares the measurements to determine if the lesion is able to block myocardial propagation.

U.S. Patent Application 2007/0198007 to Govari et al. describes a method for using pacing to assess a lesion created by ablation. The method monitors intracardiac ablation progress by evaluating a pacing signal that is captured while ablation energy is directed to intracardiac tissue. The ablation is considered to be successful by failing to capture the signal while the signal is generated at a maximum predetermined pacing voltage.

U.S. Patent Application 2015/0038824 to Lupotti describes a system configured to assess the formation of lesions both during and after ablation of tissue. The system includes an emitter that conveys electromagnetic radiation to tissue, thereby causing the tissue to responsively generate a photoacoustic wave. The system also includes an ultrasound transducer that generates a signal indicative of a characteristic of the tissue responsive to the photoacoustic wave.

U.S. Patent Application 2007/0198007 to Govari et al. describes a method for identifying and visualizing gaps between cardiac ablation sites. The method includes receiving location of the cardiac ablation sites, measuring distances between the sites, and identifying one or more gaps between the sites.

Documents incorporated by reference in the present patent application are to be considered an integral part of the application except that to the extent any terms are defined in these incorporated documents in a manner that conflicts with the definitions made explicitly or implicitly in the present specification, only the definitions in the present specification should be considered.

The description above is presented as a general overview of related art in this field and should not be construed as an admission that any of the information it contains constitutes prior art against the present patent application.

SUMMARY OF THE INVENTION

There is provided, in accordance with an embodiment of the present invention, a method for assessment of a lesion formed between first and second regions of tissue in a body cavity, the method including using a first probe in contact with the tissue at a stimulus location in the first region, applying to the tissue or sensing in the tissue a first activation signal having a first activation peak at a first time, receiving, from a second probe having multiple electrodes in contact with the tissue at respective sensing locations in the second region, respective second activation signals having respective second activation peaks sensed by the electrodes following the first activation signal, identifying, based on a temporal relation between the first and second activation peaks and a spatial relation between the stimulus location and the sensing locations, one of the multiple electrodes proximal to a gap in the lesion, and displaying a map of the body cavity with the identified electrode marked on the map.

In some embodiments, identifying the one of the multiple electrodes may include finding a given electrode among the multiple electrodes that has a respective second activation peak closest in time after the first activation peak among the second activation signals. In one embodiment displaying the map of the body cavity with the identified electrode marked on the map may include presenting, on the map, an icon representing a distal end of the second medical probe, and highlighting the found electrode on the map.

In additional embodiments, applying the first activation signal may include applying, by an electrode affixed to the first medical probe, a pacing signal to the stimulus location. In further embodiments, the first region of the body cavity may include a heart and wherein the second region may include a blood vessel emanating from the heart. In one embodiment, sensing the first activation signal may include sensing, by the first medical probe, a natural signal at the stimulus location. In another embodiment, the second probe includes a lasso catheter having the multiple electrodes in contact with the sensing locations.

In further embodiments, the method may include performing, prior to applying to the tissue or sensing in the tissue the first activation signal, an ablation procedure on the tissue, thereby creating the lesion. In supplemental embodiments, the second probe may include multiple catheters having respective subsets of the electrodes.

In some embodiments, the first activation signal may include an initial first activation signal, wherein the first activation peak may include an initial first activation peak, wherein the sensing locations may include initial sensing locations, wherein the second activation signals may include initial second activation signals, wherein the second activation peaks may include initial second activation peaks, wherein the temporal relation may include an initial temporal relation, and wherein the spatial relation may include an initial spatial relation, and the method may include repositioning the second probe, applying to the tissue or sensing in the tissue a subsequent first activation signal having a subsequent first activation peak at a second time subsequent to the first time, receiving, from the multiple electrodes in the repositioned second probe and in contact with the tissue at respective subsequent sensing locations in the second region different from the initial sensing locations, respective subsequent second activation signals having respective subsequent second activation peaks sensed by the electrodes following the subsequent first activation signal, determining a probable location for a locus of the gap based on the initial temporal and the initial spatial relations, a subsequent temporal relation between the subsequent first and the subsequent second activation peaks, and a subsequent spatial relation between the stimulus location and the subsequent sensing locations, and displaying the map of the body cavity with the determined probable location of the gap marked on the map.

There is also provided, in accordance with an embodiment of the present invention, an apparatus for assessment of a lesion formed between first and second regions of tissue in a body cavity, the apparatus including a first medical probe including a first electrode, a second medical probe including multiple second electrodes, a display, and a processor configured to apply to or to sense from the first electrode in contact with the tissue at a stimulus location in the first region, a first activation signal having a first activation peak at a first time, to receive, from the second electrodes in contact with the tissue at respective sensing locations in the second region, respective second activation signals having respective second activation peaks sensed by the electrodes following the first activation signal, to identify, based on a temporal relation between the first and second activation peaks and a spatial relation between the stimulus location and the sensing locations, one of the multiple electrodes proximal to a gap in the lesion, and to present, on the display, a map of the body cavity with the identified electrode marked on the map.

There is additionally provided, in accordance with an embodiment of the present invention, a computer software product for assessment of a lesion formed between first and second regions of tissue in a body cavity and operated in conjunction with first and second medical probes for insertion into a body cavity, the product including a non-transitory computer-readable medium, in which program instructions are stored, which instructions, when read by a computer, cause the computer to use the first probe in contact with the tissue at a stimulus location in the first region for applying to the tissue or sensing in the tissue a first activation signal having a first activation peak at a first time, to receive, from the second probe having multiple electrodes in contact with the tissue at respective sensing locations in the second region, respective second activation signals having respective second activation peaks sensed by the electrodes following the first activation signal, to identify, based on a temporal relation between the first and second activation peaks and a spatial relation between the stimulus location and the sensing locations, one of the multiple electrodes proximal to a gap in the lesion, and to display a map of the body cavity with the identified electrode marked on the map.

BRIEF DESCRIPTION OF THE DRAWINGS

The disclosure is herein described, by way of example only, with reference to the accompanying drawings, wherein:

FIG. 2 is a schematic pictorial illustration of a distal end of the integrated catheter, in accordance with an embodiment of the present invention;

FIG. 3 is a schematic pictorial illustration of a distal end of the mapping catheter, in accordance with an embodiment of the present invention;

DETAILED DESCRIPTION OF EMBODIMENTS

During an ablation procedure, a lesion can be created on ostial tissue in order to prevent electrical signals from traveling between a heart (also referred to herein as a first region of tissue) and a blood vessel such as a pulmonary vein (also referred to herein as a second region of tissue). However, there may be instances when the lesion has a gap which enables electrical signals to travel from the heart to the blood vessel.

Embodiments of the present invention provide methods and systems for assessing a lesion formed between first and second regions of tissue in a body cavity. As described hereinbelow, a first activation signal is applied to the tissue or is sensed in the tissue by a first probe in contact with the tissue at a stimulus location in the first region, the first activation signal having a first activation peak at a first time. While applying or sensing the first activation signal, second activation signals are received from a second probe having multiple electrodes in contact with the tissue at respective sensing locations in the second region, the respective second activation signals having respective second activation peaks sensed by the electrodes following the first activation signal. Based on a temporal relation between the first and second activation peaks and a spatial relation between the stimulus location and the sensing locations, one of the multiple electrodes proximal to a gap in the lesion can be identified, and a map of the body cavity with the identified electrode marked on the map can be displayed.

The identified electrode is typically proximal to an area of the tissue that was not successfully ablated. Therefore, systems implementing embodiments of the present invention can help a medical professional identify an area of body cavity tissue that can be targeted for re-ablation.

System Description

Figure 1:
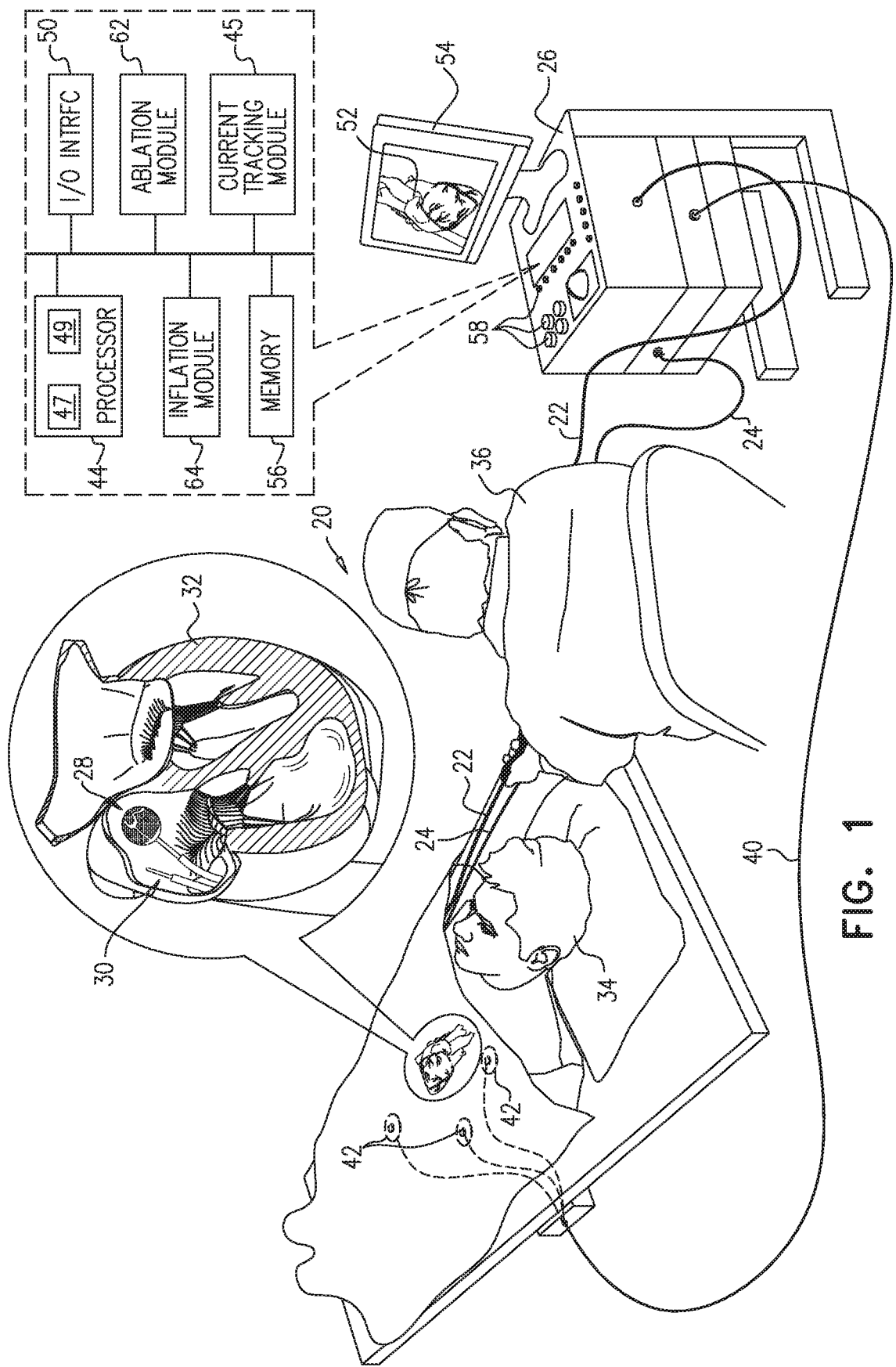
FIG. 1 is a schematic, pictorial illustration of a medical system comprising an integrated catheter and a mapping catheter, in accordance with an embodiment of the present invention.

FIG. 1 is a schematic, pictorial illustration of a medical system 20 comprising medical probes 22, 24 and a control console 26, FIG. 2 is a schematic pictorial illustration of a distal end 28 of medical probe 24, and FIG. 3 is a schematic pictorial illustration of a distal end 30 of medical probe 22, in accordance with an embodiment of the present invention. Medical system 20 may be based, for example, on the CARTO® system, produced by Biosense Webster Inc. (Irvine, Calif., U.S.A.). In embodiments described hereinbelow, medical probes 22 and 24 can be used for diagnostic or therapeutic treatment, such as for performing ablation procedures in a heart 32 of a patient 34. Alternatively, medical probe 22 and 24 may be used, mutatis mutandis, for other therapeutic and/or diagnostic purposes in the heart or in other body organs.

In embodiments described herein, medical probe 22 may also be referred to as either a mapping catheter or a first probe, and medical probe 24 may be also referred to as either an integrated catheter or a second probe.

During a medical procedure, a medical professional 36 inserts medical probes 22 and 24 into respective biocompatible sheaths (not shown) that have been pre-positioned in a body cavity (e.g., a chamber of heart 32) of the patient so that distal ends 28 and 30 of the medical probes enter the body cavity. By way of example, distal end 28 of probe 24 comprises a balloon 38 (FIG. 2) that is typically formed from bio-compatible material such as polyethylene terephthalate (PET), polyurethane, Nylon, or Pebax.

Control console 26 is connected, by a cable 40, to body surface electrodes, which typically comprise adhesive skin patches 42 that are affixed to patient 34. Control console 26 comprises a processor 44 that, in conjunction with a current tracking module 45, determines position coordinates of distal end 28 inside heart 32 based on impedances measured between adhesive skin patches 42 and one or more electrodes 46 (also referred to herein as microelectrodes 46) that are attached to an exterior wall of balloon 38. While embodiments herein describe using microelectrodes 46 as location sensors, the microelectrodes may perform other tasks (e.g., measuring electrical activity of heart 32) during a medical procedure.

In conjunction with current tracking module 45, processor 44 also determines position coordinates of distal end 30 inside heart 32 based on impedances measured between adhesive skin patches 42 and an electrode 48 that is coupled to distal end 30 and is configured to function as an impedance-based position transducer. In embodiments described herein, electrode 48 can be configured to apply a signal to tissue in heart 32, and/or to measure a certain physiological property (e.g., the local surface electrical potential) at a location in heart 32. Electrode 48 is connected to control console 26 by wires (not shown) running through medical probe 22.

Processor 44 may comprise real-time noise reduction circuitry 47 typically configured as a field programmable gate array (FPGA), followed by an analog-to-digital (A/D) ECG (electrocardiograph) signal conversion integrated circuit 49. The processor can pass the signal from A/D ECG circuit 47 to another processor and/or can be programmed to perform one or more algorithms disclosed herein, each of the one or more algorithms comprising steps described hereinbelow. The processor uses circuitry 47 and circuit 49, as well as features of modules which are described in more detail below, in order to perform the one or more algorithms.

Although the medical system shown in FIGS. 1, 2 and 3 uses impedance-based sensing to measure a location of distal ends 28 and 30, other position tracking techniques may be used (e.g., techniques using magnetic-based sensors). Impedance-based position tracking techniques are described, for example, in U.S. Pat. Nos. 5,983,126, 6,456,864 and 5,944,022, whose disclosures are incorporated herein by reference. Magnetic position tracking techniques are described, for example, in U.S. Pat. Nos. 5,391,199, 5,443,489, 6,788,967, 6,690,963, 5,558,091, 6,172,499 and 6,177,792, whose disclosures are incorporated herein by reference. The methods of position sensing described hereinabove are implemented in the above-mentioned CARTO® system and are described in detail in the patents cited above.

Control console 26 also comprises an input/output (I/O) communications interface 50 that enables the control console to transfer signals from, and/or transfer signals to electrodes 46, 48 and adhesive skin patches 42. Based on signals received from electrodes 46, 48 and adhesive skin patches 42, processor 44 can generate a map 52 that shows the position of distal ends 28 and 30 in the patient's body. During the procedure, processor 44 can present map 52 to medical professional 36 on a display 54, and store data representing the map in a memory 56. Memory 56 may comprise any suitable volatile and/or non-volatile memory, such as random access memory or a hard disk drive. In some embodiments, medical professional 36 can manipulate map 54 using one or more input devices 58. In alternative embodiments, display 54 may comprise a touchscreen that can be configured to accept inputs from medical professional 36, in addition to presenting map 52.

In embodiments of the present invention, balloon 38 comprises one or more electrodes 60, that are typically used for ablation and so are also referred to herein as ablation electrodes 60, attached to the exterior wall of balloon 38. In the configuration shown in FIG. 2, ablation electrodes 60 have non-polygonal shapes, and microelectrodes 46 are positioned in "islands" within the ablation electrodes. Electrodes 46 and 60 can be fabricated with the balloon and typically comprise gold overlaying the exterior wall of balloon 38.

Control console 26 also comprises an ablation module 62, and an inflation module 64. Ablation module 62 is configured to monitor and control ablation parameters such as the level and the duration of ablation power (e.g., radio-frequency energy) conveyed to ablation electrodes 60. Inflation module 64 is configured to monitor and control the inflation of balloon 38.

In some embodiments, inflation module 64 can use irrigation fluid to inflate balloon 38, and control the inflation of the balloon by controlling a flow rate of the irrigation fluid into the balloon. In these embodiments balloon 38 typically comprises multiple small fenestrations (not shown) that allow the irrigation fluid to exit the balloon. These fenestrations are typically 0.025-0.500 millimeters in diameter.

As shown in FIG. 2, balloon 38 is formed around a tubular shaft 66 that can be manipulated by medical professional 36 in order to extend through the balloon. By way of example, tubular shaft 66 encompasses an end section 68 that is formed as a complete or partial lasso, i.e., as a preformed arcuate structure. In embodiments described herein, end section 68 may also be referred to as lasso 68.

The radius of curvature of end section 68, when unconstrained, is typically between 7.5 mm and 15 mm. Because the arc structure is resilient and, possibly, slightly helical, when end section 68 is positioned in heart 32 (or in a pulmonary vein, as described hereinbelow), the end section will press against the heart tissue or the blood vessel tissue over the entire length of the arc, thus facilitating good tissue contact. The arcuate and possibly helical shape of end section 68 may be maintained, for example, by incorporating a thin strut made from a shape memory material, such as Nitinol (not shown), in the desired shape within the end section. The strut is made sufficiently flexible to permit the end section to straighten during insertion and withdrawal through tubular shaft 66, but to resume its arcuate form when it is unconstrained inside the heart chamber.

End section 68 comprises an array of electrodes 70 distributed along the end section. Electrodes 70 may also be referred to herein as lasso electrodes 70, and have respective widths between 1 mm and 4 mm, and are spaced between 1 mm and 10 mm apart. Lasso electrodes 70 are typically used for sensing. Electrodes 46, 60 and 70 are connected to control console 26 by wires (not shown) running through medical probe 24.

Ablation Verification

Figure 4:
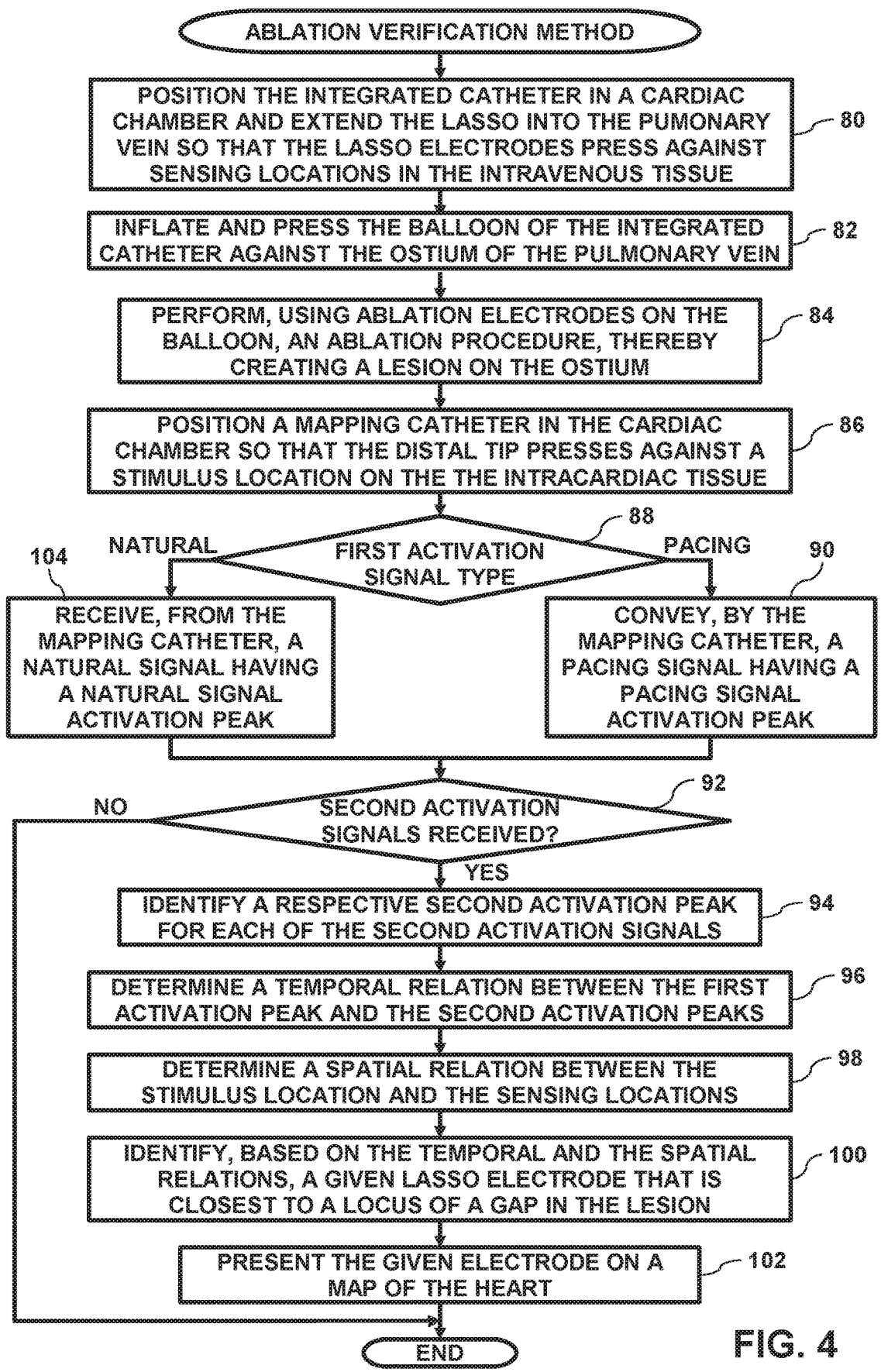
FIG. 4 is a flow diagram that schematically illustrates a method of using the integrated and the mapping catheters to verify a ablation procedure that created a lesion on ostial tissue between a cardiac chamber and a pulmonary vein, in accordance with an embodiment of the present invention.
Figure 5:
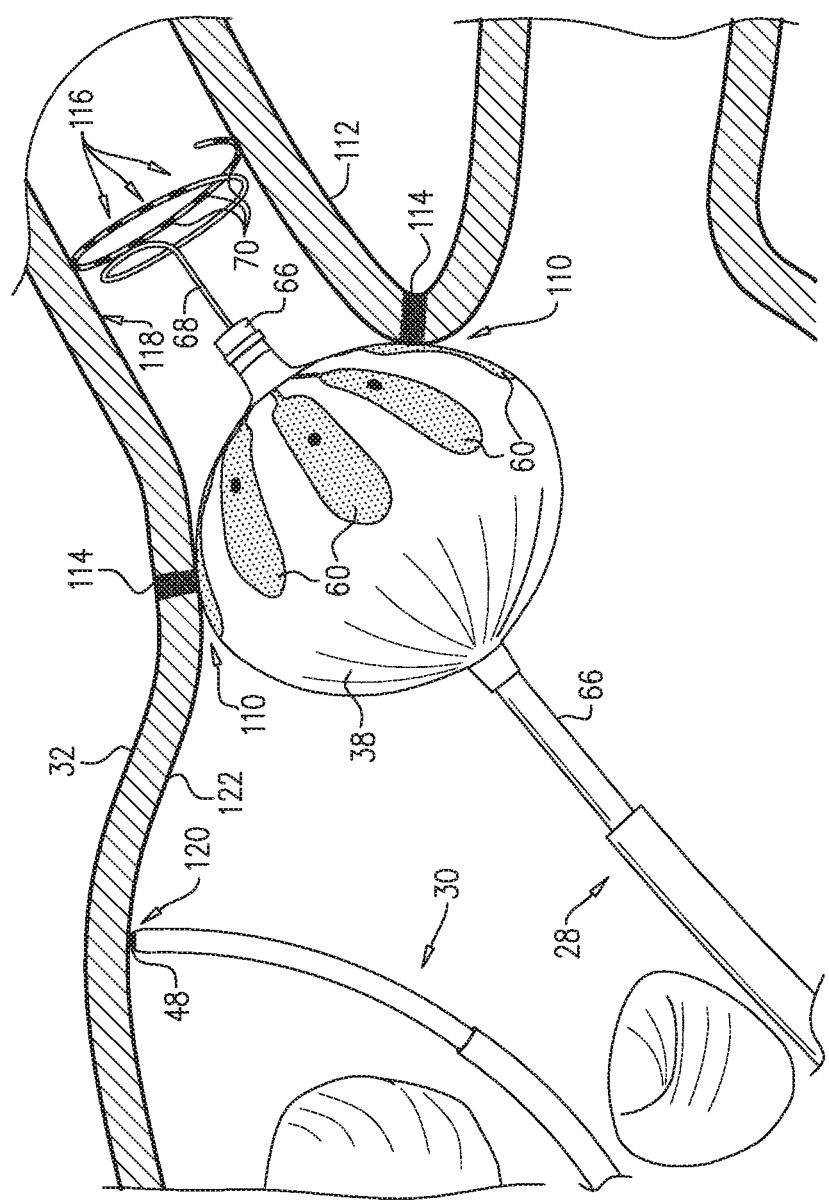
FIG. 5 is a schematic detail view of the distal ends of the integrated and the mapping catheters in the cardiac chamber and the pulmonary vein, in accordance with an embodiment of the present invention.

FIG. 4 is a flow diagram that schematically illustrates a given algorithm for performing and verifying an ablation procedure in heart 32, and FIG. 5 is a schematic detail view of distal ends 28 and 30 in heart 32 while performing and verifying the ablation procedure on ostial tissue 110 of pulmonary vein 112, in accordance with an embodiment of the present invention. As described hereinbelow, processor 44 can analyze a first and second activation signal having respective first and second activation peaks in order to identify a gap in a lesion created during an ablation procedure.

In a first positioning step 80, medical professional 36 positions distal end 28 in a chamber of heart 32, and manipulates medical probe 24 so that end section 68 extends from shaft 66. Upon extending from tubular shaft 66, section 68 forms into a lasso shape, thereby pressing lasso electrodes 70 against sensing locations 116 on intravenous tissue 118. In an inflation step 82, medical professional 36 inflates balloon 38, and manipulates medical probe 24 so that ablation electrodes 60 press against ostial tissue 110. To inflate balloon 38, medical professional 36 conveys an inflation signal (e.g., via a given input device 58) to inflation module 64, and upon receiving the inflation signal, the inflation module delivers an inflation fluid (e.g., irrigation fluid) to balloon 38, thereby inflating the balloon.

In an ablation step 84, medical professional 36 conveys an ablation signal to ablation module 62, and in response, the ablation module delivers radio-frequency (RF) energy to ablation electrodes 60, thereby performing an ablation procedure on ostial tissue 110 that creates a lesion 114. In a second positioning step 86, medical professional 36 positions distal end 30 in the chamber of heart 32, and manipulates medical probe 22 so that electrode 48 presses against a stimulus location 120 on intracardiac tissue 122. Electrode 48 may be used to inject a pacing signal into location 120 or to acquire a natural signal from the location. The pacing or natural signal is herein termed an activation signal. In a signal selection step 88, if a first activation signal comprises a pacing signal, then in a pacing step 90, medical console conveys, to stimulus location 120 on intracardiac tissue 122 (via electrode 48), a pacing signal having a pacing signal peak. If the first activation signal comprises a natural signal, i.e., a signal generated by the heart, the flow diagram continues in a step 104, described below.

In a comparison step 92, if processor 44, in conjunction with current tracking module 45 and while executing the given algorithm, receives second activation signals from lasso electrodes 70 (i.e., the lasso electrodes in contact with intravenous tissue 118), control continues to a step 94 wherein the processor identifies a respective second activation peak for each of the second signals. Steps of the flow diagram subsequent to step 94 are described below. In embodiments described herein, the second activation signals comprise signals that lasso electrodes 70 detect at sensing locations 116 in response to electrode 48 delivering the first activation signal to stimulus location 120.

Figure 6:
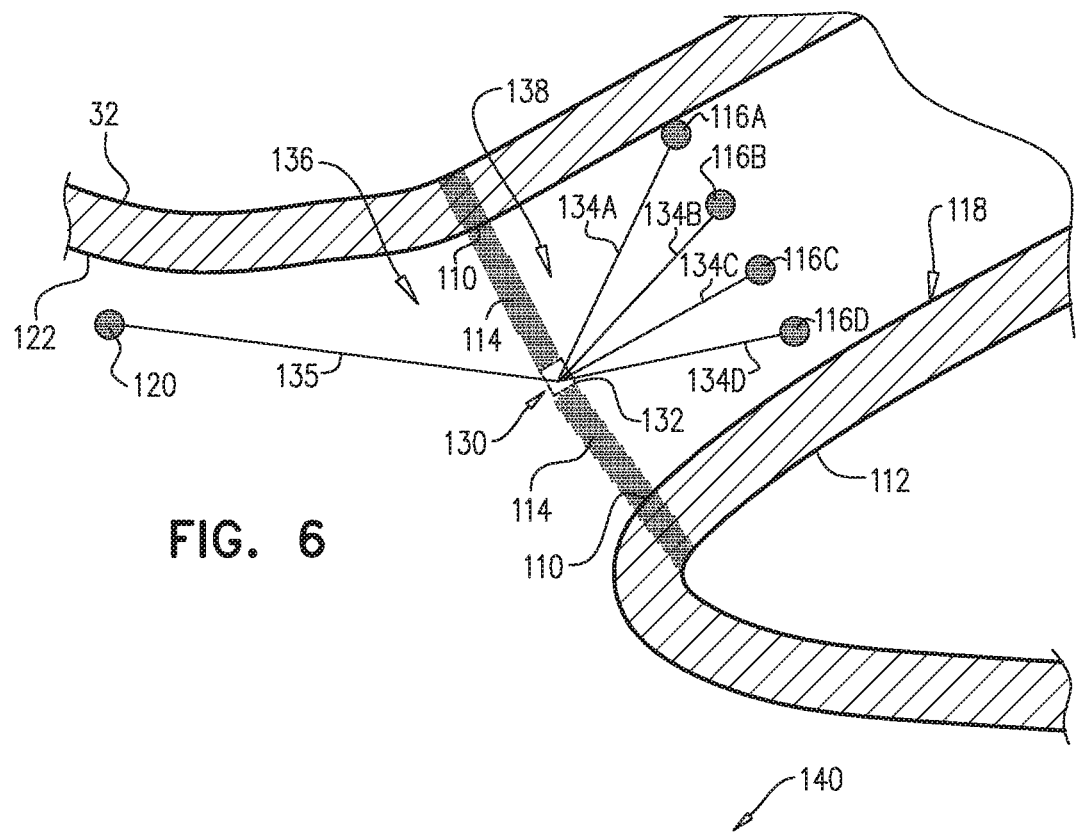
FIG. 6 is a schematic detail view of a stimulus location in the cardiac chamber and multiple sensing locations in the pulmonary vein, in accordance with an embodiment of the present invention.
Figure 7:
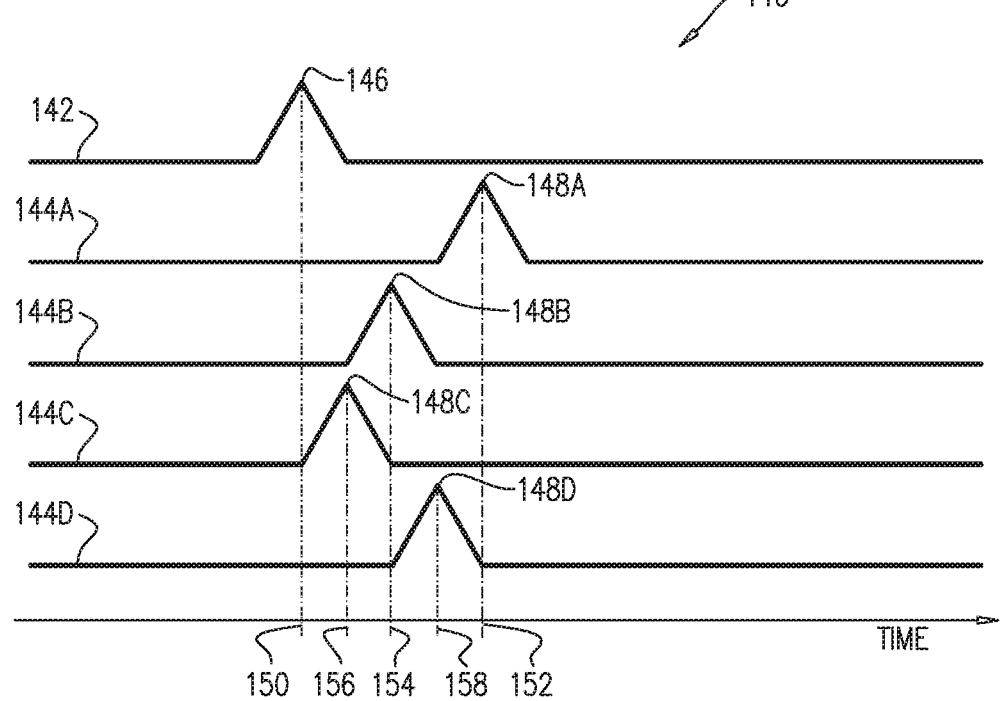
FIG. 7 is a schematic chart showing a first activation signal that is applied or sensed in the stimulus location, and second activation signals that are received from the sensing locations, in accordance with an embodiment of the present invention.

FIG. 6 is a schematic detail view of lesion 114, stimulus location 120 and sensing locations 116, and FIG. 7 is a chart 140 showing a first activation signal 142 sensed or applied by electrode 48, and second activation signals 144 detected by lasso electrodes 70, in accordance with an embodiment of the present invention. In embodiments described herein, first activation signal 142 has a first activation peak 146 at a first time, and each second activation signal 144 has a respective second activation peak 148 at a respective second time subsequent to the first time. In some embodiments, processor 44 can present, in map 52, the schematic detail view of lesion 114 (e.g., stimulus location 120 and sensing locations 116) that is shown in FIG. 6.

In FIGS. 6 and 7, sensing locations 116, second activation signals 144 and second activation peaks 148 can be differentiated by appending a letter to the identifying numeral, so that the sensing locations comprise sensing locations 116A-116D, the second activation signals comprise second activation signals 144A-144D, and the second activation peaks comprise second activation peaks 148A-148D. In embodiments described herein, a first given lasso electrode 70 detects, at sensing location 116A, second activation signal 144A having second activation peak 148A, a second given lasso electrode 70 detects, at sensing location 116B, second activation signal 144B having second activation peak 148B, a third given lasso electrode 70 detects, at sensing location 116C, second activation signal 144C having second activation peak 148C, and a fourth given lasso electrode 70 detects, at sensing location 116D, second activation signal 144D having second activation peak 148D.

Returning to the flow diagram of the given algorithm, after step 94 processor 44 determines a temporal relation between first activation peak 146 and second activation peaks 148 in a first determination step 96, and determines a spatial relation between stimulus location 120 and sensing locations 116 in a second determination step 98. In a second identification step 100, processor 44 identifies, based on the temporal and the spatial relations, a given lasso electrode 70 that is closest (i.e., of all the lasso electrodes) to a locus 130 (FIG. 6) of a presumed gap 132, i.e. a location of gap 132, in lesion 114.

In operation, processor 44 determines the spatial relation between stimulus location 120 and sensing locations 116 by first identifying stimulus location 120 and sensing locations 116. In embodiments described herein, stimulus location 120 comprises a location of mapping electrode 48 and sensing locations 116 comprise respective locations of lasso electrodes 70. In the configuration shown in FIGS. 1-3, processor 44 uses impedance-based position tracking techniques to determine the respective locations of mapping electrode 48 and lasso electrodes 70. Examples of impedance-based position tracking techniques are described in U.S. Pat. Nos. 5,983,126, 6,456,864 and 5,944,022 cited above.

In an alternative configuration, medical system 20 can use magnetic-based position tracking techniques to determine the respective locations of mapping electrode 48 and lasso electrodes 70. Examples of magnetic-based position tracking techniques are described in U.S. Pat. Nos. 5,391,199, 5,443,489, 6,788,967, 6,690,963, 5,558,091, 6,172,499 and 6,177,792 cited above.

In embodiments described herein, an ablation procedure forms lesion 114 between a first region 136 and a second region 138, and the lesion comprises gap 132 at locus 130. As described supra, electrode 48 applies or senses the first activation signal to stimulus location 120, and processor 44 receives the second activation signals from lasso electrodes 70 at respective sensing locations 116.

As shown in FIG. 6, the second activation signals detected at sensing locations 116 travel paths (i.e., from stimulus location 116) that comprise path segments 134 and 135. In the example shown in FIG. 6, a first given second activation signal detected by a first given lasso electrode 70 travels from stimulus location 120 to sensing location 116A via path segments 135 and 134A, a second given second activation signal detected by a second given lasso electrode 70 travels from stimulus location 120 to sensing location 116B via path segments 135 and 134B, a third given second activation signal detected by a third given lasso electrode 70 travels from stimulus location 120 to sensing location 116C via path segments 135 and 134C, and a fourth given second activation signal detected by a fourth given lasso electrode 70 travels from stimulus location 120 to sensing location 116D via path segments 135 and 134D.

For purposes of visual simplicity, path segments 135 and 136 are shown as straight lines radiating from a single point in gap 132. Additionally, while FIG. 6 shows, for purposes of visual simplicity, a single path segment 135 between locus 130 and stimulus location 120, the second activation signals may comprise different paths from the stimulus location to the locus of the gap.

As shown in chart 140, first activation peak 146 occurs at time 150, second activation peak 144A occurs at time 152, second activation peak 144B occurs at time 154, second activation peak 144C occurs at time 156, and second activation peak 144D occurs at time 158. By determining a temporal relation between times 150-158, and determining a spatial relation between locations 116 and 120, processor 44 can determine the closest lasso electrode to locus 130. In the example shown in chart 140, determining the given lasso electrode may comprise identifying, as the temporal relation, that second activation peak 148C is closest in time to first activation peak 146, and then determining, as the spatial relation, that locus 130 is in proximity to the given lasso electrode at sensing location 116C.

Returning to the flow diagram, in a presentation step 102, processor 44 presents, in map 52 on display 54, the given electrode, and the method ends. In one embodiment, processor 44 can overlay an icon (not shown) representing lasso 68 on map 52 and highlight a section of the icon, thereby identifying the given lasso electrode that is closest to the presumed gap in the lesion (i.e., the third given lasso electrode in the example shown in FIGS. 6 and 7). Medical professional 36 can then use the position of the identified lasso electrode to re-ablate a region, in proximity to the identified position, that typically includes gap 132.

In some embodiments, the lasso electrodes are positioned at respective locations 116 on intravenous tissue 118, and if processor 44 receives initial second activation signals 144 from the lasso electrodes (and therefore detects that gap 132 exists), medical professional 36 can reposition lasso 68 in pulmonary vein 112 so that the lasso electrodes are positioned at respective subsequent sensing locations on the intravenous tissue different from sensing locations 116. Using embodiments described herein, electrode 48 may be used to inject (or detect) a subsequent pacing signal having a subsequent first activation peak into location 120.

Once processor 44 receives subsequent second activation signals having respective subsequent second activation peaks from the repositioned lasso electrodes, the processor can determine a probable location of locus 130 (i.e., a probable location of the gap), based on (a) the temporal relation between first activation peak 146 and second activation peaks 148 and the spatial relation between stimulus location 120 and sensing locations 116, and (b) a subsequent temporal relation between the subsequent first activation peak and the subsequent second activation peaks and a subsequent spatial relation between stimulus location 120 and the subsequent sensing locations.

In one embodiment the probable location of locus 130 is a position where a sum of a first distance, between sensing location 116 to a selected region of lesion 114, and of a second distance, between a subsequent sensing location to the selected region, is a minimum. In an alternative embodiment, the sum is weighted according to a first time, between the first activation peak 146 and the closest in time second activation peak 148, and a second time, between the subsequent first activation peak and the closest in time subsequent second activation peak.

In some embodiments, processor 44 can mark, in map 52, the probable location of the locus, and present the updated (i.e., marked) map on display 54.

Returning to step 88, if the first activation signal comprises a natural signal, then in a receiving step 104, processor 44, operating in conjunction with current tracking module 45 and executing the given algorithm, receives a natural signal of heart 32 that was sensed by electrode 48, and the method continues with step 92. The natural signal has a natural signal activation peak, and in embodiments using a natural signal, the first activation peak comprises the natural signal activation peak.

Returning to step 92, if processor 44 does not receive any second activation signals from lasso electrodes 70, then the ablation procedure was successful, and the method ends.

While embodiments described herein use mapping catheter 22 and integrated catheter 24 to help identify locus 130 in ostial tissue 110 between a chamber of heart 32 and intravenous tissue 118 of pulmonary vein 112, using any number of catheters to help identify the locus of the gap in the ablation lesion in the ostial tissue between any given cardiac chamber and any blood vessel (e.g., a pulmonary artery) emanating from the given cardiac chamber is considered to be within the spirit and scope of the present invention. For example, separate catheters can be used to perform the ablation and to sense the second activation signals.

Additionally, while embodiments described herein use ablation electrodes 60 on balloon 38 to create lesion 114 and use lasso electrodes 70 (i.e., on lasso 68), using any type of ablation electrodes to create the lesion and using any type of catheter having multiple electrodes that can be simultaneously pressed against sensing locations 116 is considered to be within the spirit and scope of the present invention. Furthermore, while medical probe 24 comprises a single lasso 68 having electrodes 70 that detect the second activation signals, medical probe 24 may refer to more than one signal detection catheters, each of the signal detection catheters having respective subsets of electrodes 70.

Furthermore, while embodiments described herein can use pacing signals for detecting gap 132 in lesion 114 in heart 32, using pacing signals for detecting lesion gaps in other body organs comprising cells that can convey electrical signals is considered to be within the spirit and scope of the present invention. For example, embodiments described herein can be used to detect a gap in a lesion of the patient's brain that comprises tissue that is able to pass electrical signals between cells.

It will be appreciated that the embodiments described above are cited by way of example, and that the present invention is not limited to what has been particularly shown and described hereinabove. Rather, the scope of the present invention includes both combinations and subcombinations of the various features described hereinabove, as well as variations and modifications thereof which would occur to persons skilled in the art upon reading the foregoing description and which are not disclosed in the prior art.

The invention claimed is:

1. A method for assessment of a lesion formed between first and second regions of tissue in a body cavity, the method comprising:

using a first probe in contact with the tissue at a stimulus location in the first region, applying to the tissue or sensing in the tissue a first activation signal having a first activation peak at a first time;

receiving, from a second probe having multiple electrodes in contact with the tissue at respective sensing locations in the second region, respective second activation signals having respective second activation peaks sensed by the electrodes following the first activation signal;

identifying, based on a temporal relation between the first and second activation peaks and a spatial relation between the stimulus location and the sensing locations, one of the multiple electrodes proximal to a gap in the lesion; and displaying a map of the body cavity with the identified electrode marked on the map.

2. The method according to claim 1, wherein identifying the one of the multiple electrodes comprises finding a given electrode among the multiple electrodes that has a respective second activation peak closest in time after the first activation peak among the second activation signals.

3. The method according to claim 2, wherein displaying the map of the body cavity with the identified electrode marked on the map comprises presenting, on the map, an icon representing a distal end of the second medical probe, and highlighting the found electrode on the map.

4. The method according to claim 1, wherein applying the first activation signal comprises applying, by an electrode affixed to the first medical probe, a pacing signal to the stimulus location.

5. The method according to claim 1, wherein the first region of the body cavity comprises a heart and wherein the second region comprises a blood vessel emanating from the heart.

6. The method according to claim 1, wherein sensing the first activation signal comprises sensing, by the first medical probe, a natural signal at the stimulus location.

7. The method according to claim 1, wherein the second probe comprises a lasso catheter having the multiple electrodes in contact with the sensing locations.

8. The method according to claim 1, and comprising prior to applying to the tissue or sensing in the tissue the first activation signal, performing an ablation procedure on the tissue, thereby creating the lesion.

9. The method according to claim 1, wherein the second probe comprises multiple catheters having respective subsets of the electrodes.

10. The method according to claim 1, wherein the first activation signal comprises an initial first activation signal, wherein the first activation peak comprises an initial first activation peak, wherein the sensing locations comprise initial sensing locations, wherein the second activation signals comprise initial second activation signals, wherein the second activation peaks comprise initial second activation peaks, wherein the temporal relation comprises an initial temporal relation, and wherein the spatial relation comprises an initial spatial relation, and comprising:

repositioning the second probe;

applying to the tissue or sensing in the tissue a subsequent first activation signal having a subsequent first activation peak at a second time subsequent to the first time;

receiving, from the multiple electrodes in the repositioned second probe and in contact with the tissue at respective subsequent sensing locations in the second region different from the initial sensing locations, respective subsequent second activation signals having respective subsequent second activation peaks sensed by the electrodes following the subsequent first activation signal;

determining a probable location for a locus of the gap based on the initial temporal and the initial spatial relations, a subsequent temporal relation between the subsequent first and the subsequent second activation peaks, and a subsequent spatial relation between the stimulus location and the subsequent sensing locations; and displaying the map of the body cavity with the determined probable location of the gap marked on the map.

* * * * *